United States Patent [19]

Russie

[11] Patent Number: 5,022,395
[45] Date of Patent: Jun. 11, 1991

[54] IMPLANTABLE CARDIAC DEVICE WITH DUAL CLOCK CONTROL OF MICROPROCESSOR

[75] Inventor: Renold J. Russie, New Brighton, Minn.

[73] Assignee: Cardiac Pacemakers, Inc., St. Paul, Minn.

[21] Appl. No.: 376,511

[22] Filed: Jul. 7, 1989

[51] Int. Cl.$^5$ ............................................ A61N 1/362
[52] U.S. Cl. .............................................. 128/419 PG
[58] Field of Search ...................... 128/419 PG, 419 P

[56] References Cited

U.S. PATENT DOCUMENTS

| | | | |
|---|---|---|---|
| 4,390,020 | 6/1983 | Herpers | 128/419 PG |
| 4,390,022 | 6/1983 | Calfee et al. | 128/419 PG |
| 4,404,972 | 9/1983 | Gordon et al. | 128/419 PG |
| 4,407,288 | 10/1983 | Langer et al. | 128/419 PG |
| 4,424,812 | 1/1984 | Lesnik | 128/419 PG |
| 4,561,442 | 12/1985 | Vollmann et al. | 128/419 PG |
| 4,625,730 | 12/1986 | Fountain et al. | 128/419 D |

FOREIGN PATENT DOCUMENTS

| | | | |
|---|---|---|---|
| 0077845 | 5/1983 | European Pat. Off. | 128/419 PG |
| 3218733 | 12/1982 | Fed. Rep. of Germany | 128/419 PG |

Primary Examiner—William E. Kamm
Assistant Examiner—Kennedy J. Schaetzle
Attorney, Agent, or Firm—Fleit, Jacobson, Cohn, Price, Holman & Stern

[57] ABSTRACT

A microprocessor based implantable cardiac treatment device having first and second clocks. The first clock is a continuously running external clock of a relatively low frequency for controlling low power, uncomplicated operations of the device. The second clock runs at a much higher frequency for controlling the complex, high power operations of the microprocessor. Clock control circuitry is provided for activating the second clock only when it is determined that high power calculations are to be made by the microprocessor.

16 Claims, 5 Drawing Sheets

ONE MHz CLOCK

STOP CLOCK INHIBIT:

8 msec INHIBIT:

IMPLANTABLE CARDIAC DEVICE WITH DUAL CLOCK CONTROL OF MICROPROCESSOR

BACKGROUND OF THE INVENTION

The present invention relates to a microprocessor based implantable cardiac device, and more specifically to a microprocessor system having dual clock control to reduce the current drain of the microprocessor.

In implantable devices, such as implantable pacemakers and defibrillators, it sometimes is appropriate to provide a plurality of timing signals at various frequencies. For example, a single clock frequency can be chosen to drive a set of continuously clocked timers and the microprocessor in the implantable device, and the microprocessor can be capable of assuming either a sleep mode or a run mode. The run mode could be triggered by one of a plurality of presettable timers timing out, the occurrence of an asynchronous event such as an R-wave sense, telemetry interrupt information, etc. However, a single clock system does not provide the optimal frequency for driving either the microprocessor or each of the individual timers.

Specifically, in such systems, the frequency provided to the timers generally would be too high, if taken directly from the clock source. Therefore, the source clock signal must be divided down to drive the various presettable timers, such as for example, timing the various intervals in a pacing algorithm. This frequency division of the source clock signal is a waste of power.

In addition, to partially reduce power requirements, the frequency provided to the microprocessor by the clock source typically would be lower than that at which the microprocessor is capable of running. Therefore, either the source clock signal would have to be multiplied to a higher frequency, of the slower frequency would be used to drive the microprocessor. Under the latter situation, the microprocessor would have a slower response time to external stimuli and thus have a limited overall processing capability, particularly in the implementation of a complex computation algorithm.

SUMMARY OF THE INVENTION

It is a primary object of this invention to provide a microprocessor based control system having maximum processing capability, but not at the expense of power requirements.

It is another object of the present invention to provide a microprocessor based implantable system having dual clocks whereby a first clock is employed for basic timing functions, and a second, high powered clock is employed only for processing or computational functions performed by the microprocessor.

It is yet another object of the present invention to provide a microprocessor based implantable system having first and second separate clocks whereby a first clock is free running for performing basic timing functions, and a second clock is turned on and off only as required to perform high powered computational functions by a microprocessor.

It is a further object of this invention to provide a modified ring oscillator circuit having instant on and off control and also having the capability of being held in its high state for a predetermined period of time to prevent the microprocessor from attempting to read or write while the various other timers in the microprocessor based implantable system are changing.

The above and other objects and advantages will become more apparent when reference is made to the following description taken in conjunction with the accompanying drawings.

DETAILED DESCRIPTION OF THE DRAWINGS

Figure 1:
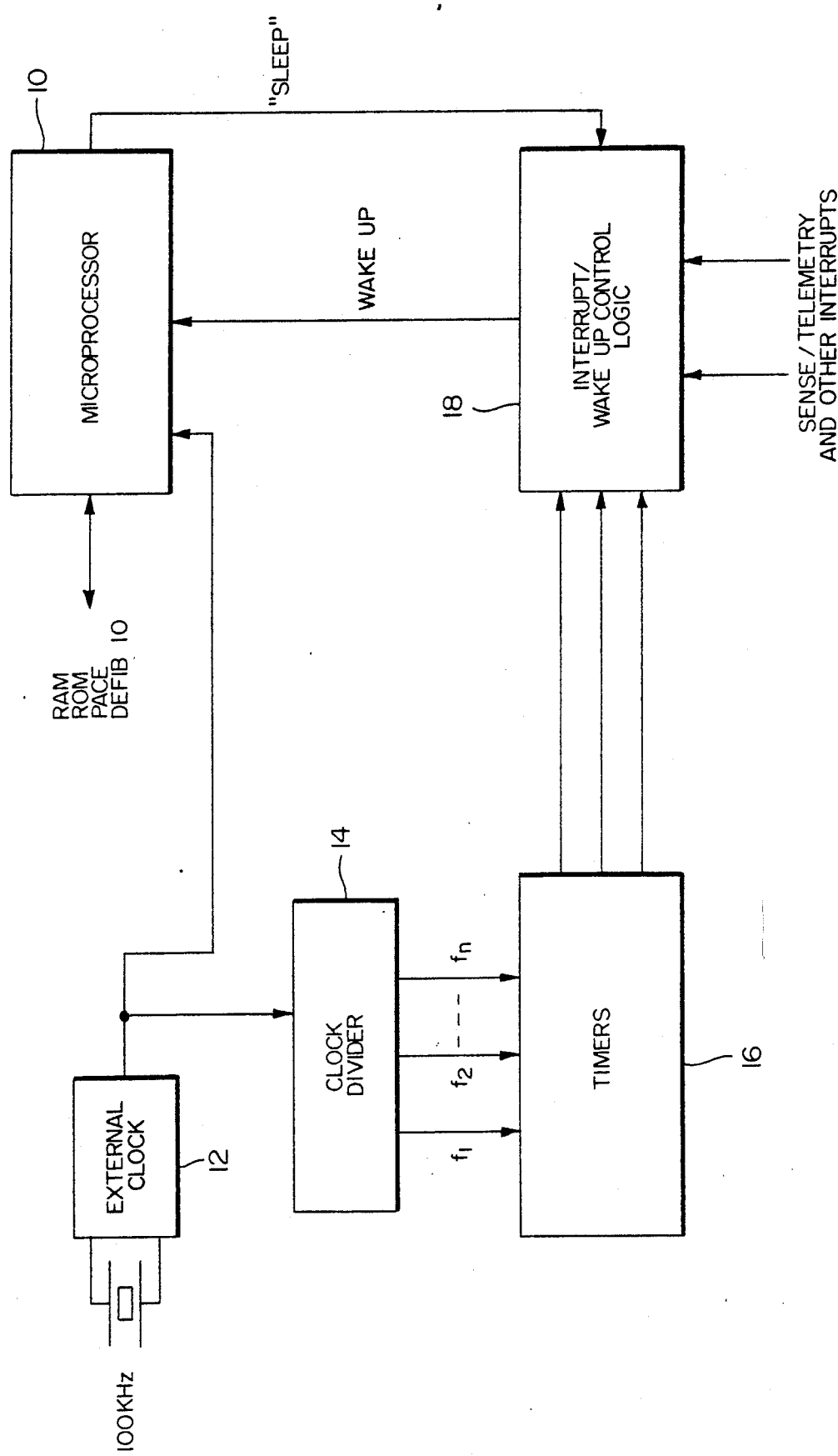
FIG. 1 is a schematic block diagram illustrating a microprocessor base control system of the prior art.

Referring first to FIG. 1, a microprocessor based implantable system of the prior art is illustrated. In this system, a microprocessor 10 is driven by an external clock 12, but only when awakened from a "sleep" mode. The timing signal from the external clock 12 is divided into a plurality of frequencies $F_1, F_2, \ldots F_N$ by a clock divider 14 for driving a plurality of timers designated by block 16. Upon the timers timing out, or the detection of an asynchronous event, or other external interrupts such as telemetry interrupts, detected by an interrupt/wake up control logic unit 18, the microprocessor 10 is triggered to "wake up" from the "sleep" mode to a "run" mode.

The microprocessor 10 is of the Motorola type and has a multiplexed address/data bus and address and data strobe signals for demultiplexing.

The disadvantages of this system lie in the single clock arrangement which limits the processing capabilities of the microprocessor 10 and requires additional power to generate the various other frequency clock signals for the timers. Typically, the frequency provided to the microprocessor is lower than that at which the microprocessor is capable of running. As a result, the microprocessor 10 has a limited processing capability and a slower response time to external stimuli. Furthermore, because the external clock frequency (100 kHz) is typically higher than that required by the individual timers, the clock divider 14 must divide the external clock signal to generate the various frequencies required for various timing algorithms, such as a pacing algorithm.

Figure 2:
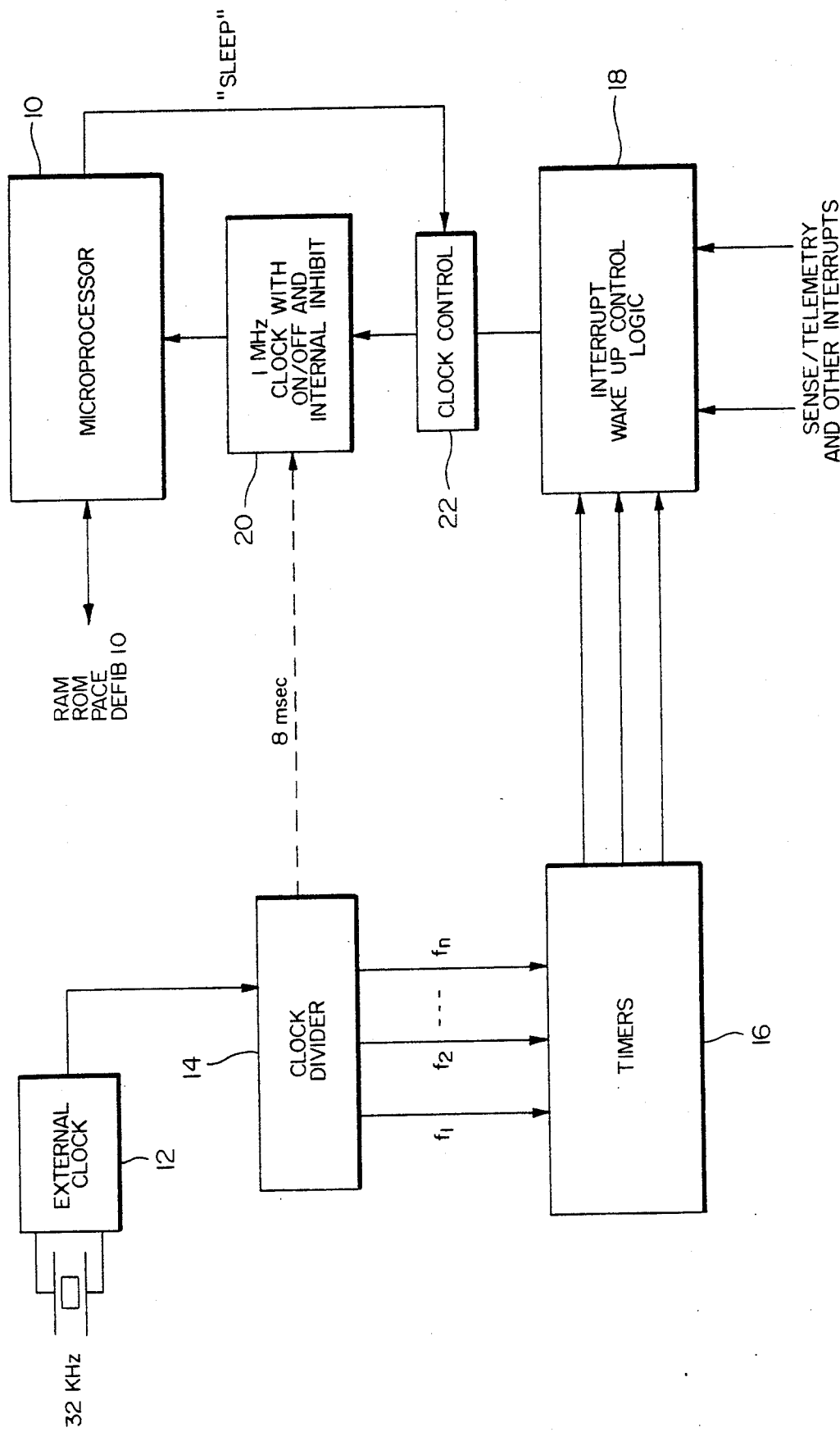
FIG. 2 is a schematic block diagram illustrating the microprocessor based control system having dual clocks, in accordance with the present invention.

Referring now to FIG. 2, where like elements from FIG. 1 are shown by the same reference numerals, the microprocessor based system in accordance with the present invention is shown. The system of FIG. 2 includes a 1 MHz clock 20 connected between the microprocessor 10 and the interrupt/wake up control logic unit 18, that serves the purpose of providing a clock signal for the microprocessor 10.

The frequencies of the clocks 12 and 20 can be optimized for a particular application. However, a 32 kHz clock 12 has been found to be suitable for basic timing functions in pacing and defibrillation in accordance with the present invention. In addition, a 1 MHz clock for the microprocessor 10 provides a ten times improvement in response time to external events and allows for more processing between events when necessary.

The external clock and the associated timers 16 are free running devices. The clock 20 on the other hand, is turned on and off only as required. Typically, the events which will trigger the clock 20 to turn on include the timing out of one of the timers 16, the detection of an asynchronous event, the sensing of a predetermined cardiac condition, or telemetry interrupts provided to the interrupt/wake up control logic unit 18. The logic unit 18 determines, based on the input from the timers and any other external input, whether it is necessary to employ the high level processing capabilities of the microprocessor, and as such "wake up" the clock 20.

When a condition is detected that triggers the microprocessor 10 to "wake up", the microprocessor 10 and clock 20 stay operational as long as the microprocessor 10 determines that high level computation needs exist. However, once it is determined that there is no longer a need for the microprocessor 10, the microprocessor 10 triggers the clock 20 to turn off or enter the "sleep" mode as illustrated in FIG. 2. By this arrangement, both power and processing capabilities are optimized since the high power clock 20 is only operating when high level processing capabilities are required. In addition, by providing both a low power clock 12 and a high power clock 20, the high power clock being active only when high level processing is required, the processing capabilities of the microprocessor 10 are optimized at little or no expense to power consumption. Furthermore, because the microprocessor is controlled by its own clock 20, the external clock 12 can be of a lower frequency than that of the prior art system (FIG. 1). By this, the clock divider 14 requires less power to generate the required timing signals since the source signal which the clock divider 14 receives is lower.

Figure 3:
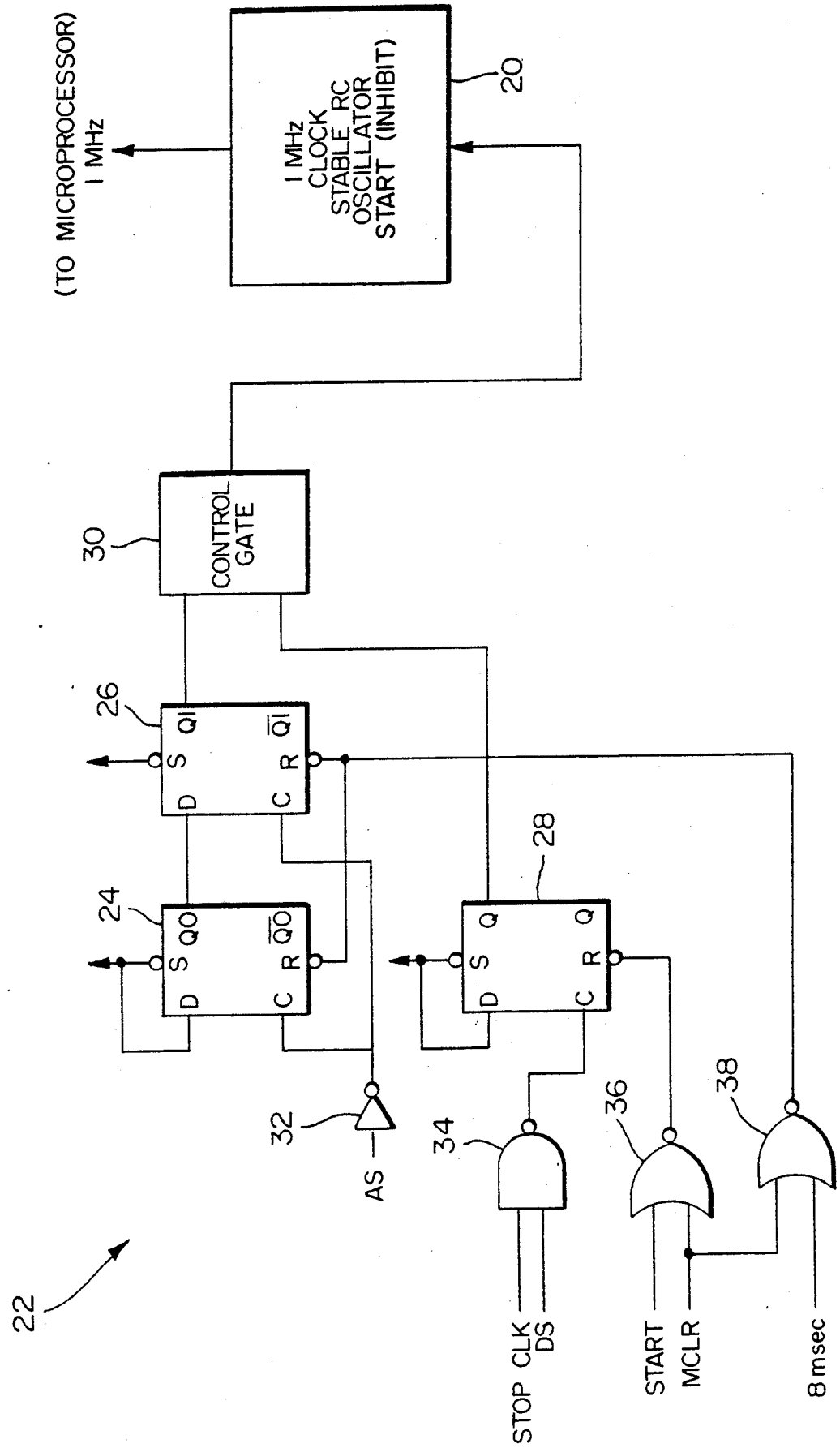
FIG. 3 is a schematic diagram illustrating the modified clock circuit having start and inhibit control in accordance with the teachings of the present invention.

Referring to FIG. 3, the clock control circuitry 22 is shown in detail and comprises three D-type flip-flops, 24, 26, and 28, and a control gate 30. The control signals include AS (Address Strobe) STOP-CLK, DS (Data Strobe), START, MCLR, and 8 msec. The 8 msec clock signal is derived from the 32KHZ clock and has a pulse width of 15 microsec, while the address strobe AS is derived from the 1 MHz clock by the microprocessor. The signal AS is connected to the clock inputs of flip-flops 24 and 26 via inverter 32. The STOP-CLK and DS signals are connected to the clock input of flip-flop 28 via the NAND gate. START and MCLR are fed the reset terminal of flip-flop 28 via the NOR gate 36. Finally, the 8 msec signal together with MCLR are connected via NOR gate 38 to the reset terminals of flip-flops 24 and 26.

The control gate 30 inhibits the clock 20 upon the occurrence of either input to the gate 30 being high. The MCLR signal is the master clear signal which goes high upon system power up or when a clear of the system is initiated by an external reset. The 8 msec signal is a clock that is fed to the system timer to clock them at 128 Hz. The 8 msec signal is derived from the 32KHZ clock signal and has a pulse width of 15 microsec.

Figure 4:
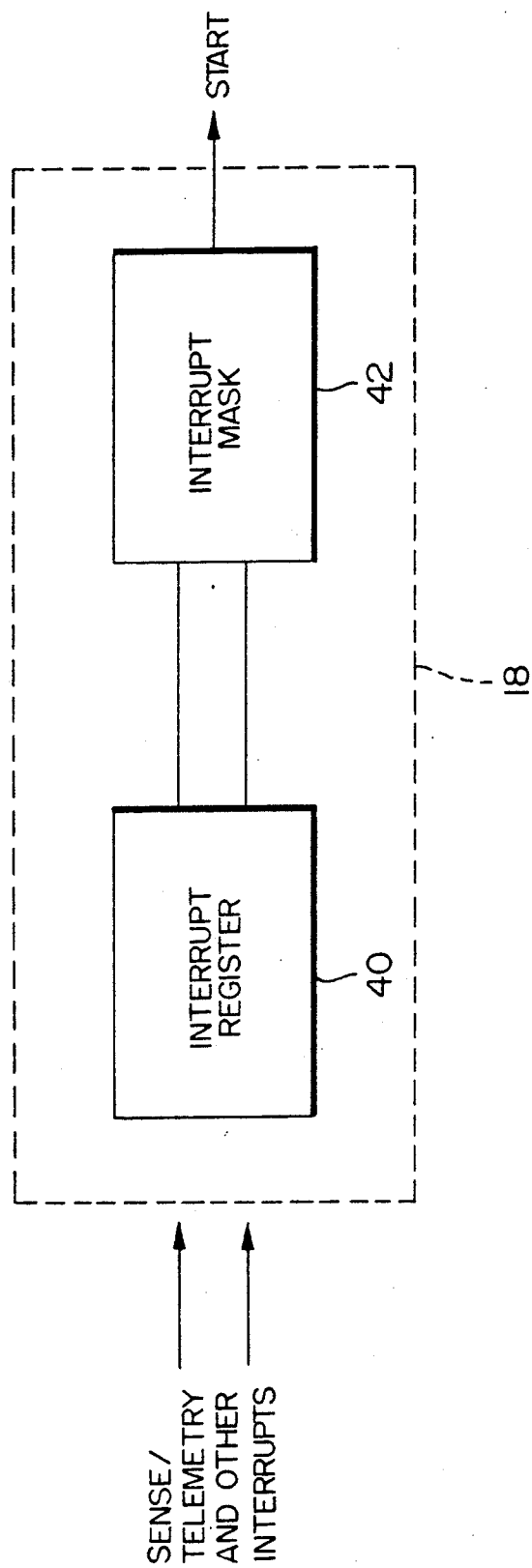
FIG. 4 is a schematic diagram of the interrupt and clock start circuity.

The control circuitry 22 responds to both signals from the microprocessor 10, which include DS, AS, and STOP-CLK, and to other externally generated signals, such as START, 8 msec and MCLR. The START signal triggers the clock 20 to its state and is generated as a result of programmable interrupts stored in an interrupt register 40, as shown in FIG. 4. The contents of interrupt register 40 is compared, bit by bit, with the contents of an interrupt mask 42. If a programmed interrupt is not masked by the interrupt mask 42, then the START signal is generated.

The STOP-CLK signal, which terminates operation of the clock 20, is generated by the microprocessor 10 when reference to a particular address in an internal program is made. The STOP-CLK signal interrupts operation of the clock 20 and freezes the clock in its off state. System software for the microprocessor 10 is written to respond to input from the timers 16 or other interrupts and then to turn off the clock 20.

Figure 5:
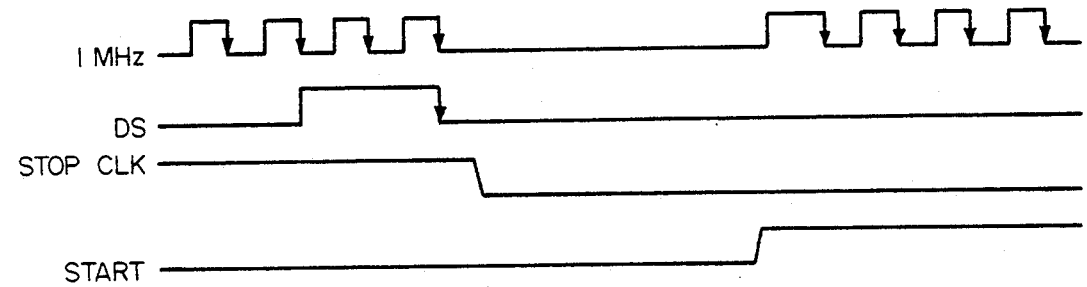
FIG. 5 is a timing diagram illustrating the various signals and their correlation in the stop clock inhibit mode.
Figure 6:
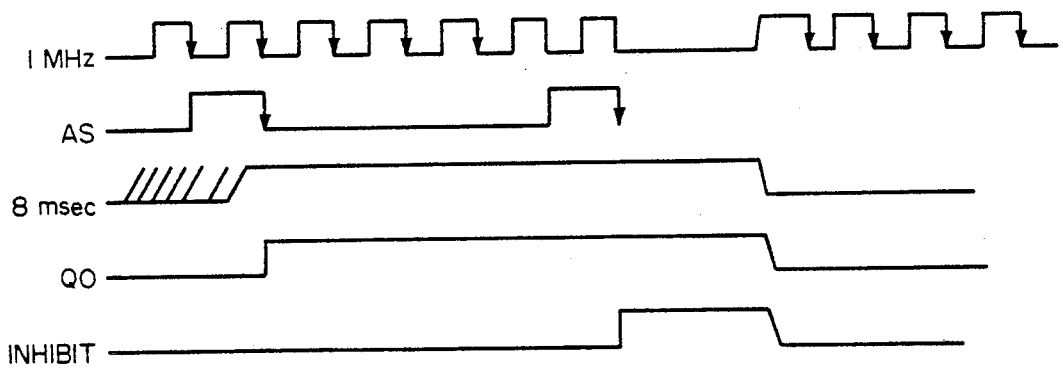
FIG. 6 is a timing diagram illustrating the timing signals and their correlation in the predetermined time interval inhibit mode.

Referring now to FIGS. 3, 5 and 6, the operation of the control circuitry 22 will be described. FIG. 5 illustrates the operation of clock 20 in response to START and STOP-CLK signals. The 1 MHz clock signal corresponds to the output of clock 20. As illustrated, output of the ring oscillation based clock 20 is immediately terminated when the STOP-CLK signal goes from high to low. The clock 20 turns on when the START signal goes from low to high.

FIG. 6 illustrates the timing for the clock inhibit mode whereby the operation of clock 20 is suspended to prevent the microprocessor 10 from reading the value of the timers 16 while they are being clocked by a 128 Hz clock signal. The 8 msec clock is the primary clock to the timers. This signal is a pulse one-half the width of the 32KHZ clock cycle which occurs every 7.8125 msec. The timers are clocked on the falling edge of the 8 msec clock and the inhibit circuit 22 is inactive as long as the 8 msec is low. This is accomplished by holding flip-flops 24 and 26 in Reset states. When the 8 msec signal goes high, the Reset on these flip-flops is released. At the trailing edge of the first pulse of the Address Strobe AS following the transition from 0 to 1 of the 8 msec clock, flip-flop 24 is clocked triggering the output Q0 to logic 1. Thus, a logic 1 is applied to the data input of flip-flop 26. At the second AS pulse, the output of flip-flop 26 Q1 goes high which holds the microprocessor in the address decode state until the 8 msec clock goes to low. Thus, it is guaranteed that 3 microseconds will be provided from the time the timers are clocked until the first high to low transition of the Data Strobe DS, when data is written or read. The flip-flops 24 and 26 provide a synchronizing mechanism between the 8 msec clock signal, which is derived from the 32 KHz clock, and the Address Strobe As, which is derived from the 1 MHz clock. Synchronization is required between these two asynchronous signals for proper cooperation of the two clocks.

The above description is intended by way of example only and is not intended to limit the present invention in any way except as set forth in the following claims.

I claim:

1. An implantable microprocessor cardiac based device comprising:

microprocessor means for determining one of a plurality of cardiac treatment therapies;

external clock means for continuously generating a clock signal of a first frequency;

auxiliary clock means for generating a clock signal of a second frequency for controlling said microprocessor means, said auxiliary clock means being capable of assuming an active state for generating said clock signal of said second frequency, and an inactive state whereby no clock signal is generated;

interrupt decision means for setting the state of said auxiliary clock means;

clock control means for triggering said auxiliary clock means to assume one of said active or inactive states under control of said interrupt decision means and said microprocessor means;

a plurality of timer means capable of producing as output, time-out signals to said interrupt decision means and said microprocessor means;

clock divider means for receiving as input said clock signal of said first frequency and generating as output a plurality of clock signals at a plurality of different frequencies to said plurality of timer means; and means to synchronize said external clock means and said auxiliary clock means so that said plurality of timer means are in a stable state when the microprocessor means reads said time-out signals.

2. The device of claim 1, wherein said first frequency generated by said external clock means is substantially slower than the second frequency generated by said auxiliary clock means.

3. The device of claim 1, wherein said microprocessor means controls said clock control means to trigger said auxiliary clock means to assume said inactive state.

4. The device of claim 1, wherein said clock signal of said first frequency is 32 KHz and said clock signal of said second frequency is 1 MHz.

5. A microprocessor based implantable cardiac treatment device comprising:

microprocessor means for determining one of a plurality of cardiac treatment therapies;

cardiac sensing means for sensing the electrical activity of the heart;

external clock means for continuously generating a clock signal of a first frequency;

clock divider means for receiving as input said clock signal of said first frequency and for generating as output a plurality of clock signals at different frequencies;

a plurality of timer means for receiving as input said plurality of clock signals and producing as output time-out signals capable of being read by said microprocessor means;

auxiliary clock means for generating a clock signal of a second frequency for controlling said microprocessor means, said auxiliary clock means being capable of assuming an active state for generating said clock signal at said second frequency, and an inactive state whereby no clock signal is generated;

interrupt decision means for setting the state of said auxiliary clock means, said interrupt decision means receiving as input the output of said plurality of timer means and information related to the electrical activity of the heart as sensed by said cardiac sensing means;

clock control means for triggering said auxiliary clock means to assume one of said active or inactive states under control of said interrupt decision means and said microprocessor means; and means to synchronize said external clock means and said auxiliary clock means so that said plurality of timer means are in a stable state when the microprocessor means reads said time-out signals.

6. The device of claim 5, wherein said clock signal of said first frequency is 32 KHz and said clock signal of said second frequency is 1 MHz.

7. An implantable microprocessor based cardiac device comprising:

microprocessor means for performing computations for determining one of a plurality of cardiac treatment therapies;

cardiac sensing means for sensing the electrical activity of the heart and producing an output signal representative thereof;

external memory means connected to said microprocessor means for storing information related to said plurality of cardiac treatment therapies;

external clock means for continuously generating a clock signal at a first frequency;

clock divider means for receiving as input said clock signal of said first frequency and for generating as output a plurality of clock signals at different frequencies;

a plurality of timer means for receiving as input said plurality of clock signals and producing as output time-out signals capable of being read by said microprocessor means;

auxiliary clock means for generating a clock signal at a second frequency for controlling said microprocessor means, said auxiliary clock means being capable of assuming an active state for generating said clock signal at said second frequency, and an inactive state whereby no clock signal is generated;

interrupt register means for receiving as input at least said output signal of said cardiac sensing means and said output from said plurality of timer means and for storing interrupt information for triggering said auxiliary clock means to assume said active state;

interrupt mask means connected to said interrupt register means for selectively inhibiting said interrupt information;

clock control means for receiving as input at least said output of said interrupt mask means and central signals from said microprocessor means for triggering said auxiliary clock means to assume one of said active or inactive states; and means to synchronize said external clock means and said auxiliary clock means so that said plurality of timer means are in a stable state when the microprocessor means reads said time-out signals.

8. The device of claim 7, wherein said clock signal of said first frequency is 32 KHz and said clock signal of said second frequency is 1 MHz.

9. An implantable microprocessor based cardiac device comprising:

cardiac sensing means for sensing the electrical activity of the heart and producing output signals representative thereof;

cardiac treatment means for delivering a plurality of cardiac treatments to the heart in the form of electrical stimulation signals;

microprocessor means for determining one of said plurality of cardiac treatments and controlling said cardiac treatment means accordingly;

external clock means for continuously generating a clock signal of a first frequency;

clock divider means for receiving as input said clock signal of said first frequency and for generating as output a plurality of clock signals at different frequencies;

a plurality of timer means for receiving as input said plurality of clock signals and producing as output time-out signals capable of being read by said microprocessor means;

auxiliary clock means for generating a clock signal of a second frequency for controlling said microprocessor means, said auxiliary clock means being capable of assuming an active state for generating said clock signal at said second frequency, and an inactive state whereby no clock signal is generated;

interrupt decision means for setting the state of said auxiliary clock means, said interrupt decision means receiving as input the output of said plurality of timer means and information related to the electrical activity of the heart as sensed by said cardiac sensing means;

clock control means for triggering said auxiliary clock means to assume one of said active or inactive states under control of said interrupt decision means and said microprocessor means; and means to synchronize said external clock means and said auxiliary clock means so that said plurality of timer means are in a stable state when the microprocessor means read said time-out signals.

10. The device of claim 9, wherein said clock signal of said first frequency is 32 KHz and said clock signal of said second frequency is 1 MHz.

11. An implantable microprocessor based cardiac device comprising:

cardiac sensing means for sensing the electrical activity of the heart and producing output signals representative thereof;

cardiac treatment means for delivering a plurality of cardiac treatments to the heart in the form of electrical stimulation signals;

microprocessor means for determining one of said plurality of cardiac treatments and controlling said cardiac treatment means accordingly;

external memory means connected to said microprocessor means for storing information related to said plurality of cardiac treatment therapies;

external clock means for continuously generating a clock signal at a first frequency;

clock divider means for receiving as input said clock signal of said first frequency and for generating as output a plurality of clock signals at different frequencies;

a plurality of timer means for receiving as input said plurality of clock signals and producing as output time-out signals capable of being read by said microprocessor means;

auxiliary clock means for generating a clock signal at a second frequency for controlling said microprocessor means, said auxiliary clock means being capable of assuming an active state for generating said clock signal at said second frequency, and an inactive state whereby no clock signal is generated;

interrupt register means for receiving as input at least said output signal of said cardiac sensing means and said output from said plurality of timer means and for storing interrupt information for triggering said auxiliary clock means to assume said active state;

interrupt mask means connected to said interrupt register means for selectively inhibiting said interrupt information;

clock control means for receiving as input at least said output of said interrupt mask means and central signals from said microprocessor means for triggering said auxiliary clock means to assume one of said active or inactive states; and means to synchronize said external clock means and said auxiliary clock means so that said plurality of timer means are in a stable state when the microprocessor means reads said time-out signals.

12. The device of claim 11, wherein said clock signal of said first frequency is 32 KHz and said clock signal of said second frequency is 1 MHz.

13. An implantable microprocessor based cardiac device comprising:

microprocessing means generating control signals including an address strobe signal, a data strobe signal, and a stop clock signal;

external clock means for continuously generating a clock signal of a first frequency;

clock divider means for generating a control clock signal of a predetermined frequency different from said first frequency of said clock signal;

auxiliary clock means for generating a clock signal of a second frequency for controlling said microprocessor means when said microprocessor means performs complex computations, said auxiliary clock means being capable of assuming an active state for generating said clock signal of said second frequency and an inactive state during which no clock signal is generated;

interrupt decision means for setting the state of said auxiliary clock means and generating a start clock signal upon determining to set the auxiliary clock to an active state; and clock control means for triggering said auxiliary clock means to assume one of said active or inactive states under control of said interrupt decision means and said microprocessor means, said clock control means comprising:

a NAND gate circuit receiving as input said stop clock signal and said data strobe signal;

a first NOR gate receiving as input said start clock signal and a master clear signal indicative of system power up of the cardiac device;

a second NOR gate receiving as input said master clear signal and said control clock signal of a predetermined frequency;

a control gate having first and second inputs and an output connected to said auxiliary clock means for maintaining said auxiliary clock means in an inactive state so long as a signal on either of said first and second inputs is high and otherwise causing said auxiliary clock to be in said active state;

first, second and third D-type flip-flops each having a clock input, a data input, a et input, a reset input, and an output;

said first D-type flip-flop receiving on its clock input an output of said NAND gate, receiving on its reset input an inverted output of said first NOR gate, the data input of said first D-type flip-flop being inverted and connected to said set input of said first D-type flip-flop, the output of said first D-type flip-flop being connected to the first input of said control gate;

said second D-type flip-flop receiving on its clock input an inversion of said address strobe signal, receiving on its reset input the inversion of the output of said second NOR gate, the data input of said second D-type flip-flop being inverted and connected to the set input of said second D-type flip-flop, the output of said second D-type flip-flop being connected to the data input of said third D-type flip-flop; and said third D-type flip-flop receiving on its clock input an inversion of said address strobe, receiving on its reset input the inversion of the output on said second NOR gate, the output of said third D-type flip-flop being connected to said second input of said control gate.

14. The device of claim 13, wherein said first frequency generated by said external clock means is substantially lower than the second frequency generated by said auxiliary clock means.

15. A microprocessor based implantable cardiac treatment device comprising:

cardiac sensing means for sensing the electrical activity of the heart;

microprocessor means for determining one of a plurality of cardiac treatment therapies in response to the sensed electrical activity of the heart and generating control signals including an address strobe signal, a data strobe signal, and a stop clock signal;

external clock means for continuously generating a clock signal of a first frequency;

clock divider means for receiving as input said clock signal of said first frequency and for generating as output a plurality of clock signals at different frequencies including a control clock signal at a predetermined frequency;

a plurality of timer means for receiving as input said plurality of clock signals and producing as output a time-out signal;

auxiliary clock means for generating a clock signal of a second frequency for controlling said microprocessor means when said microprocessor means performs computations, said auxiliary clock means being capable of assuming an active state for generating said clock signal at said second frequency and an inactive state during which no clock signal is generated;

interrupt decision means for setting the state of said auxiliary clock means, said interrupt decision means receiving as input the output of said plurality of timer means and information related to the electrical activity of the heart as sensed by said cardiac sensing means and generating a start clock signal upon determining to activate said auxiliary clock means; and clock control means for triggering said auxiliary clock means to assume one of said active or inactive states under control of said interrupt decision means and said microprocessor means, said clock control means comprising:

a NAND gate circuit receiving as input said stop clock signal and said data strobe signal;

a first NOR gate receiving as input said start clock signal and a master clear signal indicative of system power up of the cardiac device;

a second NOR gate receiving as input said master clear signal and said control clock signal of a predetermined frequency;

a control gate having first and second inputs and an output connected to said auxiliary clock means for maintaining said auxiliary clock means in an inactive state so long as a signal on either of said first and second inputs is high and otherwise causing said auxiliary clock to be in said active state;

first, second and third D-type flip-flops each having a clock input, a data input, a set input, a reset input, and an output;

said first D-type flip-flop receiving on its clock input an output of said NAND gate, receiving on its reset input an inverted output of said first NOR gate, the data input of said first D-type flip-flop being inverted and connected to said set input of said first D-type flip-flop, the output of said first D-type flip-flop being connected to the first input of said control gate;

said second D-type flip-flop receiving on its clock input an inversion of said address strobe signal, receiving on its reset input the inversion of the output of said second NOR gate, the data input of said second D-type flip-flop being inverted and connected to the set input of said second D-type flip-flop, the output of said second D-type flip-flop being connected to the data input of said third D-type flip-flop; and said third D-type flip-flop receiving on its clock input an inversion of said address strobe, receiving on its reset input the inversion of the output on said second NOR gate, the output of said third D-type flip-flop being connected to said second input of said control gate.

16. The device of claim 15, wherein said first frequency generated by said external clock means is substantially slower than the second frequency generated by said auxiliary clock means.

* * * * *